United States Patent [19]

Baskas

[11] Patent Number: 4,995,870
[45] Date of Patent: Feb. 26, 1991

[54] DISPOSABLE SYRINGE WITH RETRACTABLE NEEDLE

[76] Inventor: Morris J. Baskas, 200 California Rd. #14, Bronxville, N.Y. 10708

[21] Appl. No.: 520,733

[22] Filed: May 9, 1990

[51] Int. Cl.⁵ .............................................. A61M 5/00
[52] U.S. Cl. .................................. 604/110; 604/195; 604/263
[58] Field of Search ............... 604/195, 187, 198, 263, 604/110, 218, 220

[56] References Cited

U.S. PATENT DOCUMENTS 2,607,343  8/1952  Sarver .................................. 604/220
4,813,936  3/1989  Schroeder ........................... 604/195

FOREIGN PATENT DOCUMENTS 8801072  11/1989  Netherlands ......................... 604/263

Primary Examiner—John D. Yasko

[57] ABSTRACT

A safety syringe comprises a needle releasably lockable at the syringe outlet. The needle has means such as a barb for engaging and catching to a syringe plunger when the plunger is depressed to inject the syringe contents into a patient. After loosening the needle, retraction of the plunger will withdraw the needle safely into the safety of the syringe barrel.

13 Claims, 7 Drawing Sheets

DISPOSABLE SYRINGE WITH RETRACTABLE NEEDLE

This invention relates to syringes for medical or dental use for injecting medicaments into human patients.

BACKGROUND OF INVENTION

The medical and dental professions are deeply concerned about the problem of patient and professional infection. Especially does the problem exist in connection with medicament injections into a patient infected with a communicable disease, such as Aids or hepatitis. The current practice is to break off the used needle from the used syringe in a special device which stores the removed used needles in an inaccessible compartment. The remaining syringe is discarded. However, problems can still arise if the medical or dental practitioner forgets to use this special device to remove used needles from the syringe, or the special device is not immediately available.

SUMMARY OF INVENTION

The principal object of the invention is a novel syringe which provides retraction of the needle after use within the protective confines of the syringe barrel.

In accordance with one aspect of the invention, the syringe needle is provided with means for connecting the needle to the syringe plunger in such manner that withdrawal of the plunger carries the needle into the syringe barrel.

In accordance with another aspect of the invention, the needle is provided with means for locking it to the syringe barrel outlet end or nozzle, and with means when unlocked for coupling the needle end to the syringe plunger.

In a preferred embodiment, the internal needle end is provided with multi-dimensional means in the form of an enlargeable end portion, and the plunger bottom has an aperture through which the enlargeable portion can pass but only in one direction, the plunger aperture being covered by a puncturable membrane. Means are provided to lock the needle to the syringe nozzle while the plunger is depressed to extrude the barrel contents. At the end of its stroke, the enlargeable needle end punctures the membrane and enters a region above the plunger bottom. The enlargeable end is configured so that it no longer can pass through the aperture. When the needle is unlocked, withdrawal of the plunger causes the needle to retract completely and safely within the barrel. The hub is then tightened, the plunger depressed, and the syringe can then be discarded, and there is no easy way possible to cause the needle to once again project in an unsafe manner from the barrel.

A further embodiment includes a holder for use with a syringe to assist the user in assembling and disassembling the syringe.

SUMMARY OF DRAWINGS

Other objects and advantages will be apparent from the detailed description that follows of several different embodiments of the invention, taken in conjunction with the accompanying drawings wherein.

DETAILED DESCRIPTION OF PREFERRED EMBODIMENTS

Figure 1:
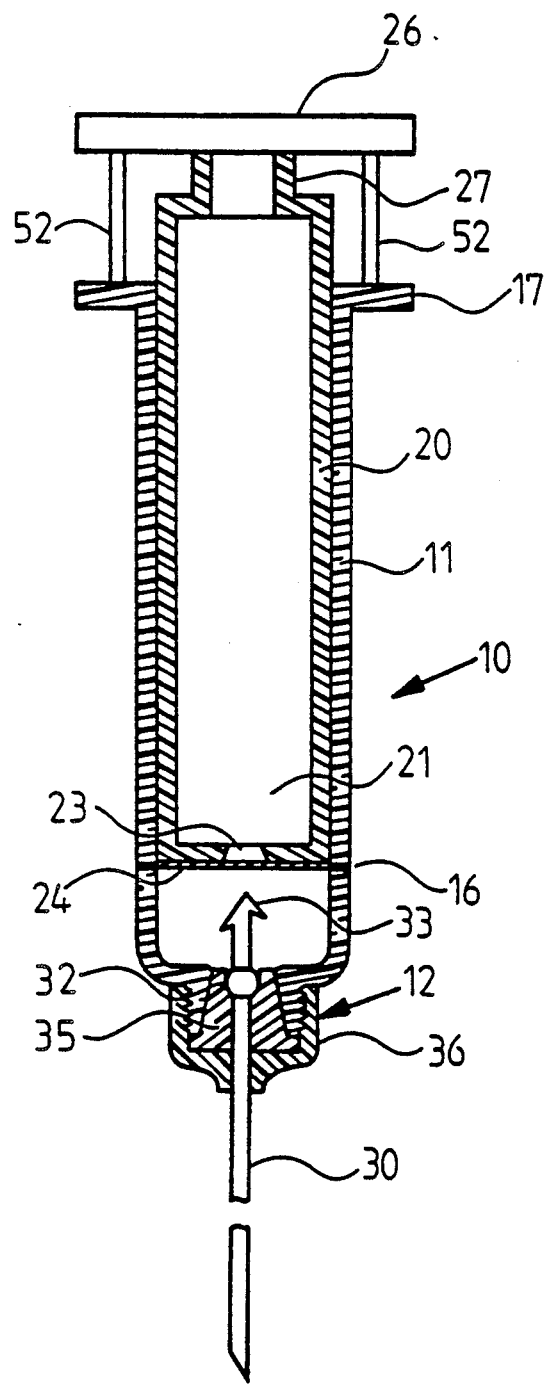
FIG. 1 is a cross-sectional view of one form of assembled syringe in accordance with the invention prior to filling the syringe with the medicaments.
Figure 2:
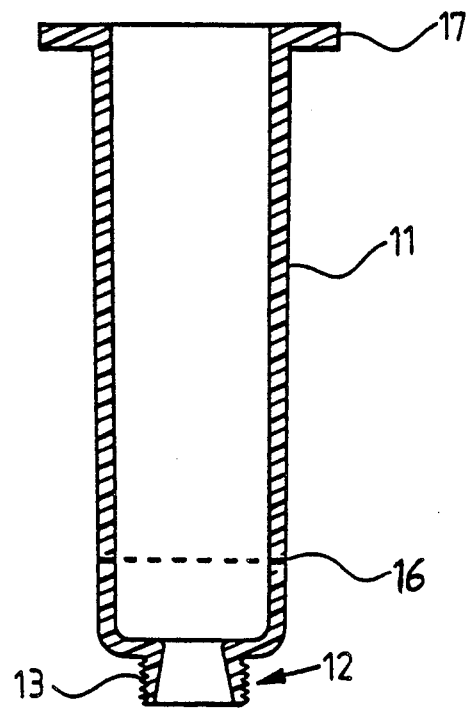
FIGS. 2-6 are cross-sectional views of the several parts of the assembly of FIG. 1.
Figure 3:
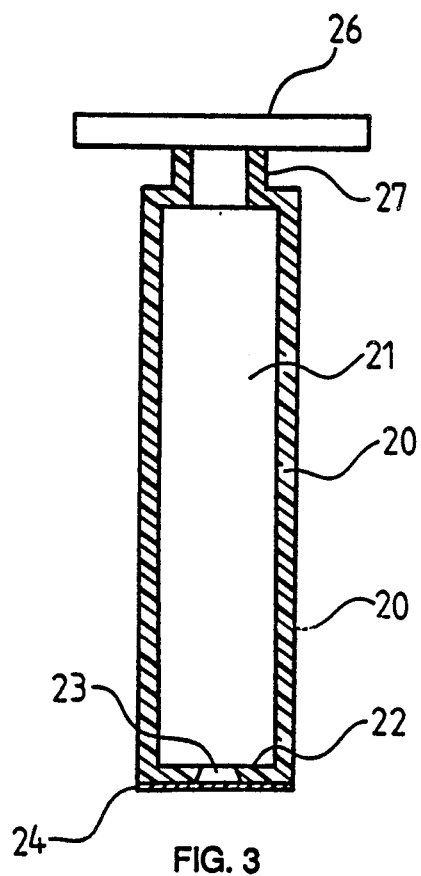
Figure 4:
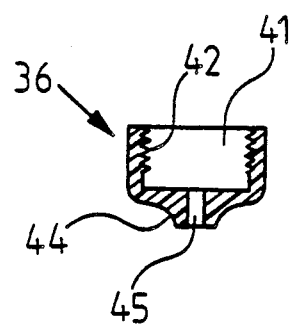
Figure 5:
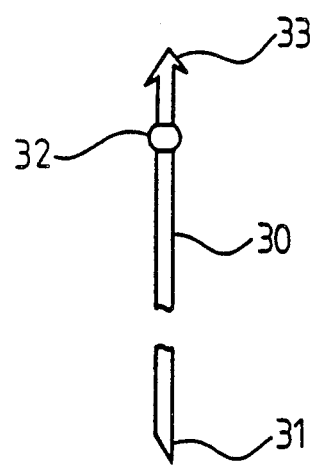
Figure 6:
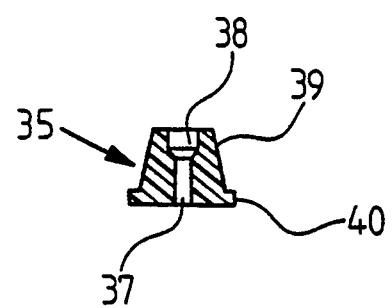

FIG. 1 shows one embodiment of a disposable syringe 10 according to the invention, prior to filling with the medicaments, and FIGS. 2-6 show the several parts of which the assembly is constituted.

The syringe 10 comprises a barrel 11, typically of plastic and typically cylindrical. The barrel 11 comprises at its lower end an outlet end 12 comprising a reduced-diameter section having an external thread 13 and a slightly tapered internal channel 14. A scribe line or other marking 16 is located about one-eighth of the distance up from the outlet end 12. The barrel 11 has at its upper end the usual flange 17 used as a finger grip by the user. A plunger 20 is configured to be slideable within the barrel 11, in a reasonably tight fit. In this embodiment, the plunger is hollow forming an internal compartment 21. The plunger bottom comprises a wall 22 having an aperture 23. Adhered to the bottom of the wall 22 is a rubber diaphragm or membrane 24 which is air and liquid tight and seals off the aperture 23. The membrane 24 is puncturable. The upper end of the plunger has the usual top 26 seated on a reduced diameter neck 27 that allows the plunger 20 to be depressed downward into the barrel 11, or retracted upward out of the barrel by the user.

A thin elongated needle 30 with a pointed end 31 and a central bore (not shown) is provided. The needle 30 differs from the usual syringe needle in having an intermediate ball-shaped enlarged portion 32, and at its upper end an enlargeable barb or spring steel tines 33 that are flexible but point downward as shown.

The needle 30 is removably supported in the outlet end 12 of the barrel by means of a rubber plug 35 and a screw-on hub 36. The plug 35 has a bore 37 with an upper outwardly tapered section 38 configured to receive the ball 32 on the needle. The plug also has a slightly tapered outer surface 39 and a bottom flange 40. The hub comprises a generally cylindrical cavity 41 having an internal thread 42, and a nozzle shaped lower portion 44 with an aperture 45 sized to receive the needle 30 in a reasonably tight fit that will allow the needle to be freely displaceable through the aperture 45.

In use, the needle comes typically in a package with the plug 35 and the ball 32 seated in the cavity 38 surrounded by the hub 36. Surrounding the needle and mounted on the hub would be a cap or cover (not shown but described below). The user inserts the hub 36 carrying the needle from the bottom into the aperture 14 of the barrel. The aperture 14 is sized to allow the barbed end 33 of the needle to pass into the barrel. The plug flange 40 seats against the bottom end 50 of the outlet 12. The user then screws the hub 36 onto the barrel outlet end 12. The latter, being of plastic, is slightly flexible, and screwing of the cap causes the reduced diameter end to be compressed, compressing in turn the rubber plug against the needle ball 32 until the needle 30 is locked to the outlet end. This is the assembled position shown in FIG. 1.

Figure 7:
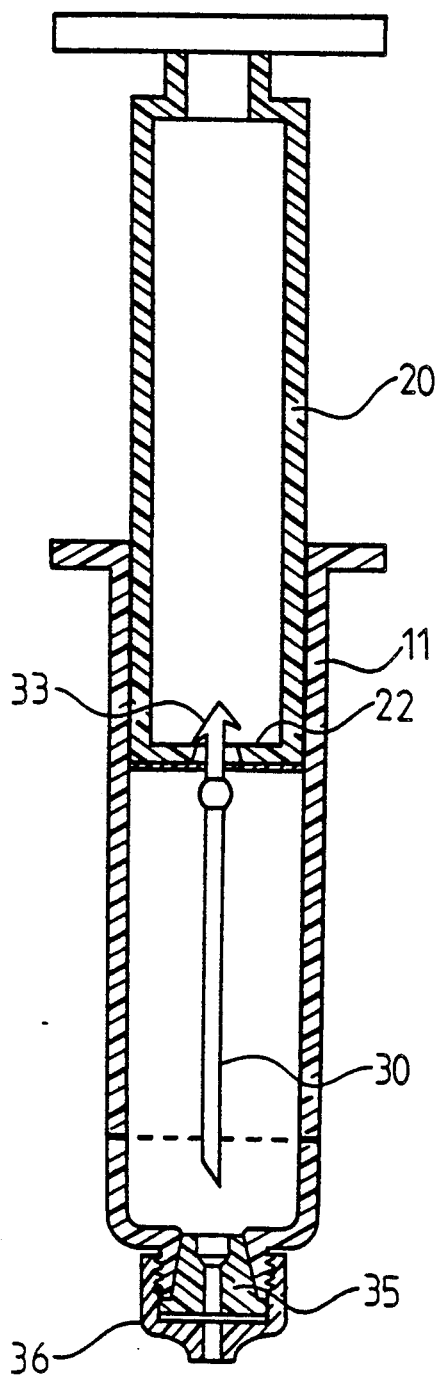
FIG. 7 is a cross-sectional view showing retraction of the needle after injection of the medicaments.

As will be noted, the height of the needle 30 is chosen such that in the assembled position it is located below the barrel scribe line 16. What is not shown in FIG. 3, but is shown in FIG. 1 are two detachable temporary struts 52 which are detachably connected to the plunger flange 26 and project downward so as to engage the barrel flange 17 and prevent the plunger bottom 24 from being depressed below the scribe line 16. A removable band can be substituted for the struts 52. In the position shown, the practitioner would then operate the syringe in the normal way, which is to depress the plunger to the position shown in FIG. 1, insert the needle into the medicament source (not shown), withdraw into the barrel the desired medicament dosage following markings not shown on the barrel surface, and then extrude a small amount of the contents to ensure all air has been displaced. When the syringe is thus ready to use on the patient, the practitioner breaks off and removes the temporary struts 52, inserts the needle into the patient, and depresses the plunger until the bottom end 24 engages the reduced diameter section at the barrel bottom, thereby injecting the full barrel contents into the patient. In this process, the barreled needle end 33 penetrates the rubber diaphragm 24, passes through the aperture 23, folding or bending if necessary to do this, and comes to rest inside the plunger compartment 21. The barbed needle end 33, after passing through the aperture 23 is restored to its original size, which is now too large to pass through the aperture 23 in the opposite direction. The practitioner now loosens the hub 36, which removes the plug pressure and unlocks the needle. When now the plunger 20 is retracted, the barbs 33 catch on the wall 22 as shown in FIG. 7, and the needle 30, now connected to the plunger lower end, is withdrawn into the safety of the barrel 11, with its end no longer projecting from the syringe and unable to cause harm to another person. The hub 36 can now be tightened. There is no reasonable way that the needle can now be forced out of its safe position. When the plunger is again depressed, the needle can't pass through the plug and will be forced upward into the plunger. The ball 32 diameter can be chosen smaller than the aperture 23, so that when the plunger is again depressed, the ball will pass through the aperture and no downward pressure is exerted on the needle. The rubber plug 37 bore can be made narrow enough so that the needle could not of its own weight pass through it, yet would allow the needle to be pushed through during assembly. Alternatively, with a larger ball diameter, after the needle has been retracted into the barrel and the hub retightened, if the plunger is again depressed, the compressed plug will prevent the needle from passing through. So long as the plunger remains within the barrel, complete protection exists against infection from a possible contaminated needle. The depressed plunger with the needle safely inside can be locked by any suitable means, such as with a rubber cap.

It is not necessary that the user assemble the needle, plug and cap to the barrel. The assembly can be made at the factory and the assembly then sterilized and sealed in a package with the struts 52 in place. Then, all the user need do is loosen the cap after the injection to allow retraction of the needle.

The invention is not limited to a hollow plunger 20 with a compartment 21. The plunger can alternatively consist of a solid upper portion with a bottom wall that contains an aperture through which the needle barbed end can pass in one direction only. Also, any needle end construction that can be narrowed to pass through the aperture 33, and then will enlarge to prevent the reverse passage can be substituted. Thus, any spring structure which flexes inward when engaging the aperture walls can be used. Similarly, the enlarged ball section 32 can have other shapes. All that is required is a structure to prevent the needle from being pushed outward under the force needed to cause the barbed end to puncture and penetrate the membrane and pass through the plunger aperture. As shown in FIG. 1, the aperture 37 will not allow the ball 32 to pass through. The ball has the advantage that, in cooperation with the concave cavity 38, it holds the needle tightly projecting forwardly along the syringe axis.

Figure 8:
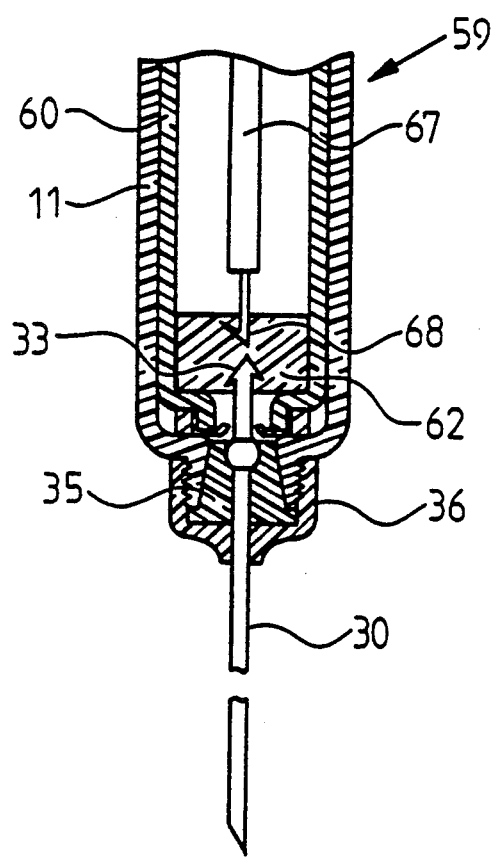
FIG. 8 is a partial cross-sectional view of another embodiment using a cartridge during needle retraction.
Figure 9:
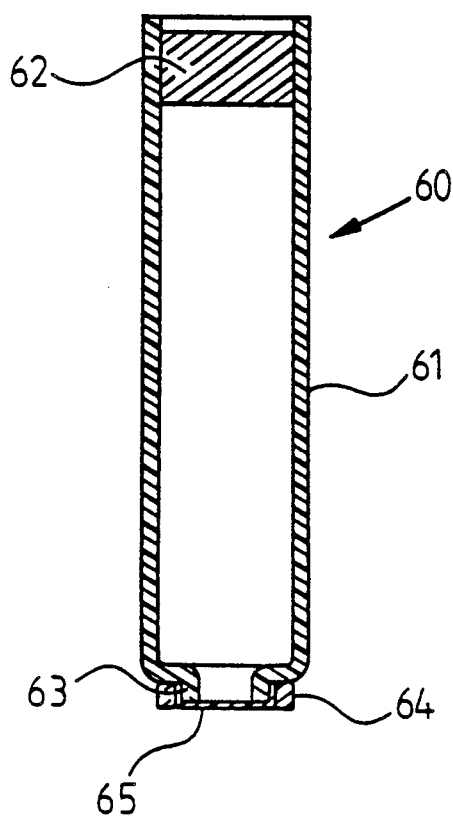
FIG. 9 is a cross-sectional view of the cartridge of the embodiment of FIG. 8.

FIGS. 8 and 9 illustrate a modification employing a conventional cartridge pre-filled with the medicament. As shown, the syringe 59 is similar to that used in the earlier embodiment, with the same reference numerals used to indicate the same parts. In this instance, however, since the syringe barrel does not have to be filled, the struts or band used to prevent barb engagement during filling of the barrel are unnecessary. The barrel 11 can be of plastic or thin metal.

The cartridge, designated 60, is conventional, and comprises a glass cylinder 61 having a rubber plunger 62 sealing off the top, and a necked-down portion 63 at the bottom surrounded by a metal band 64. A rubber diaphragm 65 seals off the bottom of the cartridge which is filled with the medicament. The cartridge 60 is placed inside the syringe barrel 11 and a conventional metal piston 67 with a barb 68 at its lower end is inserted from the top into the cartridge until it engages and hooks to the top of the rubber plunger 62. When the cartridge 60 was inserted, with the needle 30 in place, the upper end of the needle with the barb 33 punctures the cartridge diaphragm 65 and ends up in the lower part of the cartridge 60 extending above the necked-down bottom 63.

The syringe can then be used by the practitioner in the normal way. When the cartridge contents have been extruded, the rubber plunger 62 would have been pushed down to the bottom of the cartridge, and ultimately its bottom surface will engage and hook with the barb 33 at the needle top. At that point, the user loosens the hub 36, and upon retracting the piston 67 the needle, as before, is withdrawn safely into the cartridge.

Figure 10:
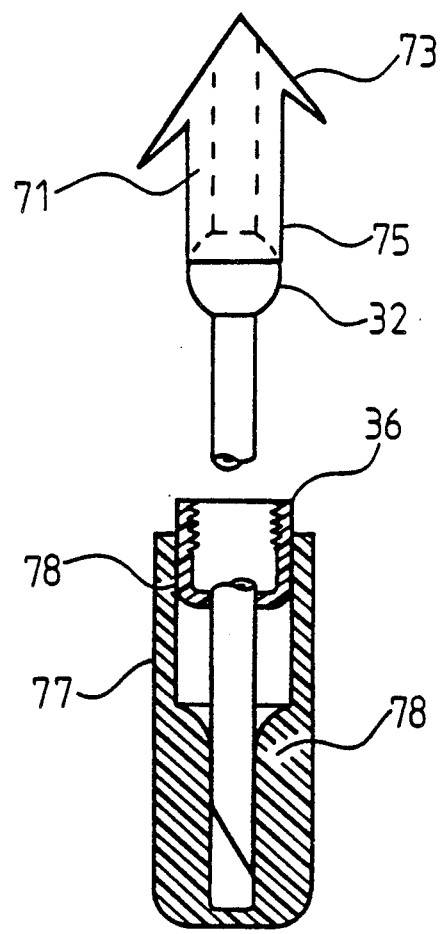
FIG. 10 is a side view of a modified needle.

FIG. 10 shows a modified needle construction 70 for very thin needles. In this case, a metal tube 71 is secured in any convenient way to the needle top, and the barb 73 is mounted on the added tube 71, because of the difficulties that may be encountered in mounting the barb on the thin needle end. This modification can if desired also be used for larger needles.

FIG. 10 also shows a further modification for simplifying withdrawal of the needle. In this case, the added metal tube 71 is extended downward 75 to cover or blend in with the enlarged ball 32. This creates a smooth tapered surface along the needle exterior from the needle top to the ball. When the needle is retracted into the barrel, that smooth exterior makes it easier for the needle to pass through the membrane at the plunger bottom in the FIG. 1 embodiment and prevents the ball catching on the membrane 65.

The needle will typically come covered with top and bottom protective sheaths for cleanliness and to prevent sticking the user. In assembling to the syringe, the top sheath would be removed and the needle positioned with its ball seated within the concavity of the plug. The user then tightens the hub to lock the needle in place. Should the ball shift upward, the user would grasp the bottom sheath 77 to pull the ball back into its seat. If the sheath does not fit snugly on the needle, allowing the needle to be pulled via the sheath, the sheath attachment can be made tighter by fitting an inside liner, shown at 78 in FIG. 10, inside the sheath. The liner 78 can be molded with the sheath 70, or alternatively the outer configuration can be tapered inward to provide the additional gripping means on the needle.

Figure 11:
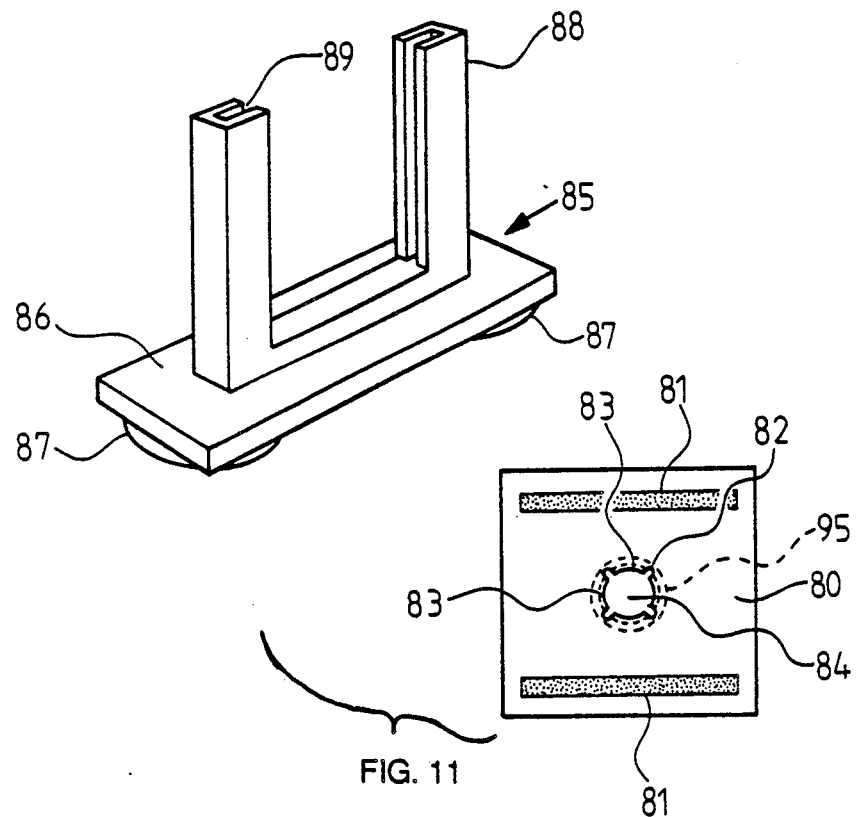
FIG. 11 is a perspective view of a packaged needle holder and card for use therewith.
Figure 12:
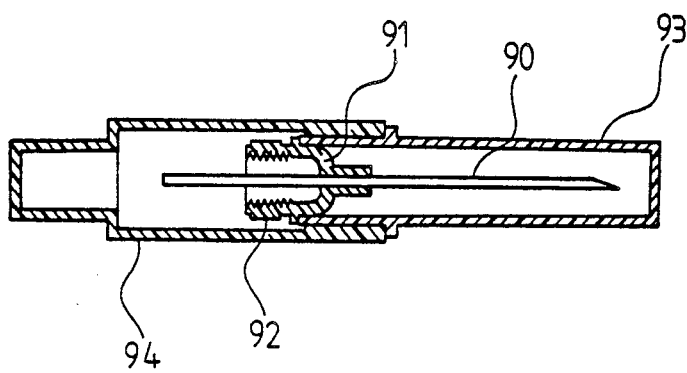
FIG. 12 is a side view of the needle with package in phantom for use with the holder of FIG. 11.

FIG. 11 shows an auxiliary device to asssist the user in mounting the needle on the syringe barrel. It has the benefit that the user need use only one hand to manage the task. This embodiment uses sterile needles that come packaged in one form of plastic sheaths as previously described, which is illustrated in FIG. 12. The hub has four circumferentially spaced ridges 92. The front sheath or scabbard 93 is mounted to the hub 91. The rear sheath or scabbard 94 is mounted over the front sheath 93. For use with the packaged needle illustrated in FIG. 12, a disposable card 80 which has two lines of self-seal adhesive 81 is provided. The card 80 has a die-cut shape 82 forming four tabs 83 disposed at 90° positions as shown. The cut shape 82 will allow the center piece 84 to be pushed out. A small holder 85 comprises a base member 86 having means 87 for securing same to a surface, permanently as by screws, or temporarily as by suction cups as shown. Rising up from the base is a U-shaped member 88 having a channel 89 to receive the card with the area 82 exposed.

Figure 13:
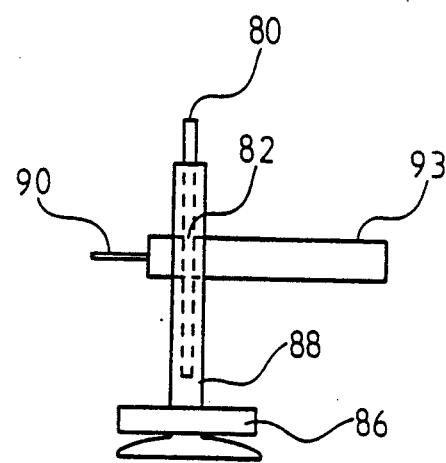
FIG. 13 illustrates the holder in use.

In operation, the user places the disposable card 80 in the channel 89 of the holder so it stands upright as shown in FIG. 13. The user then removes the rear sheath 94 from the needle and pushes the needle into the center piece 84 pushing it out and into the resultant opening 82, where it is held in place by the ridges 92 in the resilient card edges between the tabs 83. The user can then mount on the held needle hub the syringe barrel over the needle end and then rotate the barrel to tighten the hub to secure the needle in place. The user can next remove the front sheath 93 and remove the syringe from the card. After the medication has been administered, the syringe can be remounted in the card 80 after replacing the front sheath 93, and the hub loosened. When the syringe of FIG. 1 is being used, the needle can then be retracted into the barrel. In this case, though not illustrated in FIG. 12, the rubber plug 35 would have been present in the hub 91, and the needle would contain the ball 32 and barb 33, also not shown in FIG. 12. All of this can be accomplished with one hand.

In order to ensure a sufficiently tight grip between the card and the sheath, a circular rubber gasket 95 can be mounted on the card over the tabs 82, 83, with the gasket sized to grip the sheath more tightly.

The auxiliary holder is not only useful in connection with the novel syringe assembly of the invention, but also can be used with ordinary packaged sterile needles (as shown in FIG. 12) for use with conventional syringes, also in a manner to protect against accidental contamination. In this case, the card holder is used in the same manner as previously described. After use, the front sheath 93 is remounted to the exposed needle end, and the syringe mounted on the held card as before, and the syringe can be removed while the needle is held in place on the card 80. Then, the user can remove the card from the holder 85 using the sheath to hold same, and then folds the card 80 over the exposed needle rear end. The adhesive lines 81 touch and seal the exposed needle end inside the folded card. The opposite end of the needle is safely ensconsed in the sheath 93. The needle can then be safely disposed of without fear of contamination.

Figure 14:
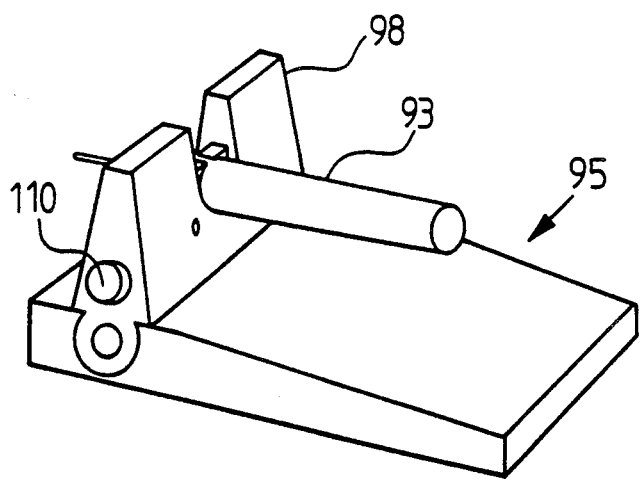
FIG. 14 is a perspective view of a modified packaged needle holder in accordance with the invention.
Figure 15:
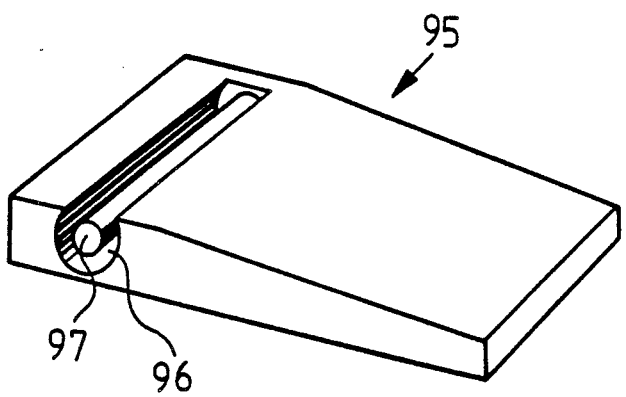
FIGS. 15-17 are views of parts of the holder illustrated in FIG. 14.
Figure 16:
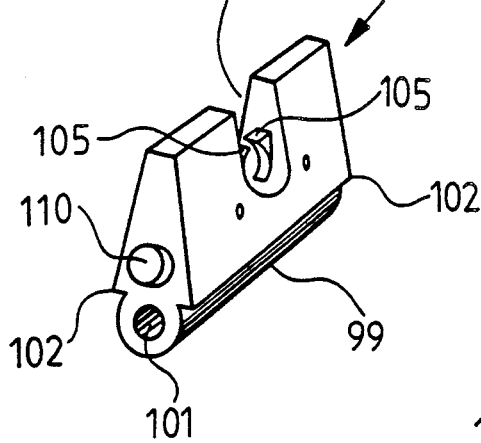
Figure 17:
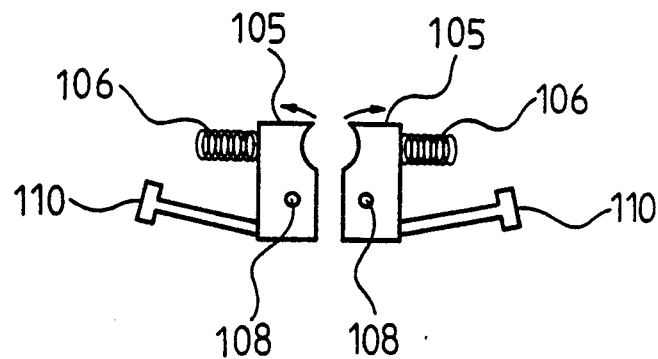

FIGS. 14–17 show a modification of the holder previously described, which does not require the card 80. In this embodiment, a base 95 is provided with a semi-cylindrical recess 96 through which a rod or pin 97, mounted on the side wall, extends. A removable stand 98, having a semi-cylindrical bottom 99 configured to fit within the recess 96 and having a center bore 101 for receiving the pin 97 is provided. As shown in FIG. 14, the stand 98 can be slid sideways into the recess 96 and will be supported in an upright position by flanges 102 on the stand.

The stand 98 is provided with a U-shaped groove 103 in whose side walls are mounted for sideways pivotable movement a pair of jaws 105. The jaws are spring-biased toward a closed or gripping position by springs 106 (see FIG. 17), and are pivotable about axes 108. Mounted in the sidewalls are a pair of slideable buttons 110 which engage the jaws below their pivot points 108. When the buttons 110 are pressed inward, the jaws open; when released, the jaws close. The jaws are configured to grip when closed the needle package end 93.

The operation is similar to the operation with the card 80. The user depresses the buttons, inserts the the needle package 93 in the open jaws and releases the buttons. The jaws 105 grip the the package, and the user can now screw on the syringe to the hub 92. Pressing the buttons 110 wil then release the syringe. After the syringe is used, the user replaces the package 93 and reinserts into the holder 98 and can then remove the syringe from the hub 92. The user can then slide out the stand 98, and over a safe receptacle depress the buttons 110 allowing the used needle to be released and fall safely into the receptacle.

It will further be evident that a slot, designated 89 in FIG. 11, to receive a card 80, can be added to the stand 98 in FIG. 14 so that the FIG. 14 embodiment will now enable the user to use either the gripper 105 or the card 80 to hold the packaged needle.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. A safety syringe for administering medicaments, comprising a barrel having an outlet end, a needle removably supported at the outlet end and having a first portion extending into the barrel and a second portion extending externally, a plunger slidably disposed within the syringe, and means on the first needle portion upon contact with the plunger for connecting to the plunger whereby upon retraction of the plunger the needle after use can be safely retracted and stored for disposable inside the syringe, said safety syringe further comprising a resilient plug mounted at the outlet end and surrounding the needle, and means for compressing the plug to lock the needle to the outlet end.

2. A syringe according to claim 1, wherein the needle comprises an enlarged portion intermediate its first and second portions.

3. A syringe according to claim 2, wherein the connecting means on the needle comprises flexible barb or spring means.

4. A syringe according to claim 1, further comprising a cartridge within the barrel, said plunger being located within the cartridge.

5. A safety syringe as claimed in claim 4, further comprising a piston with a barbed end for engaging and connecting to one side of the plunger, said needle having a barb at its first portion for engaging and connecting to the opposite plunger side.

6. A safety syringe as claimed in claim 1, further comprising an additional tube fitted over the first needle portion, said connecting means comprising a barb on the additional tube.

7. A safety syringe as claimed in claim 6, further comprising a ball on the needle, said additional tube extending to and blending in with the ball.

8. A safety syringe as claimed in claim 1, further comprising a sheath on the needle, and means for increasing the snugness of the sheath on the needle.

9. A safety syringe as claimed in claim 1, wherein the compressing means comprises a hub threadingly engaging the outlet end.

10. A safety syringe for administering medicament, comprising a cylindrical barrel having a reduced outlet end, a plunger slidably disposed within said barrel, said plunger having at its end facing the barrel outlet end an entrance aperture leading to a region behind it and a liquid-tight membrane covering the entrance aperture, a needle removable supported at the barrel outlet end and having an inner portion extending into the barrel and an outer portion projecting outwardly from the outlet end, said needle having at its inner portion multi-dimensional means capable of assuming a first narrow width capable of passing through the plunger entrance aperture and a second wider width incapable of passing through the plunger entrance aperture, said multi-dimensional means being located such that the plunger when moved into said barrel will cause said means to penetrate the membrane and pass through the entrance aperture into the region behind and assume its wider width, whereby when the plunger is retracted it will draw the needle up into the barrel such that its outer portion no longer projects from the outlet end, said safety syringe further comprising an apertured resilient plug seated in the barrel outlet end, and a hub fitted over the resilient plug and detachably secured to the outlet end for selectively compressing the resilient plug.

11. A safety syringe as claimed in claim 10, further comprising an enlarged portion on the needle seated within the apertured plug.

12. A safety syringe as claimed in claim 10, wherein the multi-dimensional means comprises a flexible structure that can be folded when traversing a boundary edge in only one direction.

13. A safety syringe as claimed in claim 10, further comprising removable means on the plunger or barrel for preventing the plunger membrane from engaging the needle end before filling the barrel with medicament.

* * * * *